United States Patent
Hwang et al.

(10) Patent No.: US 10,453,210 B2
(45) Date of Patent: Oct. 22, 2019

(54) METHOD AND APPARATUS FOR DETERMINING INTERPUPILLARY DISTANCE (IPD)

(71) Applicant: Samsung Electronics Co., Ltd., Suwon-si, Gyeonggi-do (KR)

(72) Inventors: Hyoseok Hwang, Suwon-si (KR); Hyun Sung Chang, Seoul (KR); DongKyung Nam, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 310 days.

(21) Appl. No.: 15/386,899

(22) Filed: Dec. 21, 2016

(65) Prior Publication Data

US 2017/0200285 A1    Jul. 13, 2017

(30) Foreign Application Priority Data

Jan. 8, 2016    (KR) .................. 10-2016-0002405

(51) Int. Cl.
| | |
|---|---|
| *A61B 3/11* | (2006.01) |
| *G06T 7/60* | (2017.01) |
| *G06F 3/01* | (2006.01) |
| *G06K 9/00* | (2006.01) |

(Continued)

(52) U.S. Cl.
CPC .................. *G06T 7/60* (2013.01); *A61B 3/10* (2013.01); *A61B 3/111* (2013.01); *G06F 3/013* (2013.01); *G06K 9/0061* (2013.01); *G06K 9/00604* (2013.01); *G06K 9/00912* (2013.01); *G06K 9/52* (2013.01); *G06T 2207/10004* (2013.01); *G06T 2207/10012* (2013.01); *G06T 2207/10024* (2013.01); *G06T 2207/30201* (2013.01)

(58) Field of Classification Search
CPC ............. G06T 7/60; G06T 2207/10004; G06T 2207/10012; G06T 2207/30201; G06T 19/006; A61B 3/10; G06K 9/52; G06K 9/00912; G06K 9/0061; G06K 9/00604; G06F 3/013; G02B 7/12
See application file for complete search history.

(56) References Cited

U.S. PATENT DOCUMENTS

| | | | |
|---|---|---|---|
| 7,315,415 B2 | 1/2008 | Shih-Yu et al. | |
| 8,459,792 B2 * | 6/2013 | Wilson .................... | A61B 3/111 351/204 |
| 9,025,252 B2 | 5/2015 | Lewis et al. | |

(Continued)

FOREIGN PATENT DOCUMENTS

| | | | |
|---|---|---|---|
| JP | 2004008768 A | * | 1/2004 |
| JP | 5331785 B2 | | 10/2013 |

(Continued)

OTHER PUBLICATIONS

Translated Version of JP-2004008768.*

*Primary Examiner* — Carol Wang
(74) *Attorney, Agent, or Firm* — Harness, Dickey & Pierce, P.L.C.

(57) ABSTRACT

Provided is an apparatus and method for determining an interpupillary distance (IPD), the method and apparatus may determine the IPD of a user by analyzing an image of the user gazing at a display to which a predetermined pattern is output, wherein the image may be obtained by the apparatus for determining the IPD or may be received from an external terminal.

15 Claims, 11 Drawing Sheets

(51) Int. Cl.
*G06K 9/52* (2006.01)
*A61B 3/10* (2006.01)

(56) References Cited

U.S. PATENT DOCUMENTS

| | | | | |
|---|---|---|---|---|
| 2004/0073245 | A1* | 4/2004 | Schachar | A61F 2/147 |
| | | | | 606/166 |
| 2006/0072206 | A1* | 4/2006 | Tsuyuki | G02B 27/0172 |
| | | | | 359/631 |
| 2006/0110008 | A1 | 5/2006 | Vertegaal et al. | |
| 2011/0310097 | A1* | 12/2011 | Ushio | H04N 13/261 |
| | | | | 345/419 |
| 2013/0050642 | A1* | 2/2013 | Lewis | A61B 3/113 |
| | | | | 351/204 |
| 2013/0050833 | A1* | 2/2013 | Lewis | G06K 9/00604 |
| | | | | 359/630 |
| 2013/0083003 | A1* | 4/2013 | Perez | G06F 3/005 |
| | | | | 345/419 |
| 2013/0083009 | A1* | 4/2013 | Geisner | A63F 13/02 |
| | | | | 345/419 |
| 2014/0152956 | A1* | 6/2014 | Silva | A61B 3/111 |
| | | | | 351/204 |
| 2014/0274391 | A1 | 9/2014 | Stafford | |
| 2015/0042957 | A1 | 2/2015 | Abitbol et al. | |
| 2015/0219934 | A1* | 8/2015 | Silva | A61B 3/111 |
| | | | | 351/204 |
| 2017/0180720 | A1* | 6/2017 | Jarc | G02B 21/0012 |
| 2018/0124375 | A1* | 5/2018 | Rousseau | H04N 13/344 |

FOREIGN PATENT DOCUMENTS

| | | |
|---|---|---|
| KR | 20070062617 A | 6/2007 |
| KR | 20130106537 A | 9/2013 |

* cited by examiner

600

700

800

900

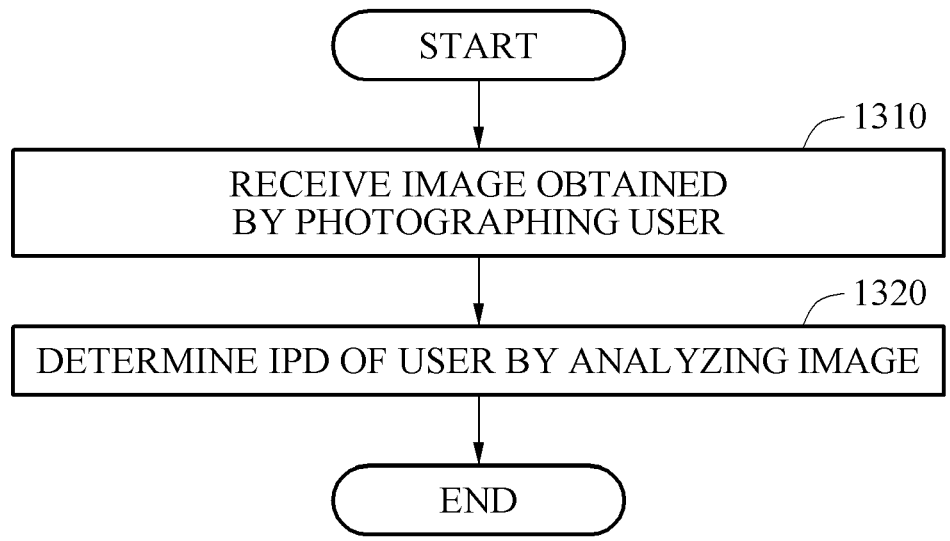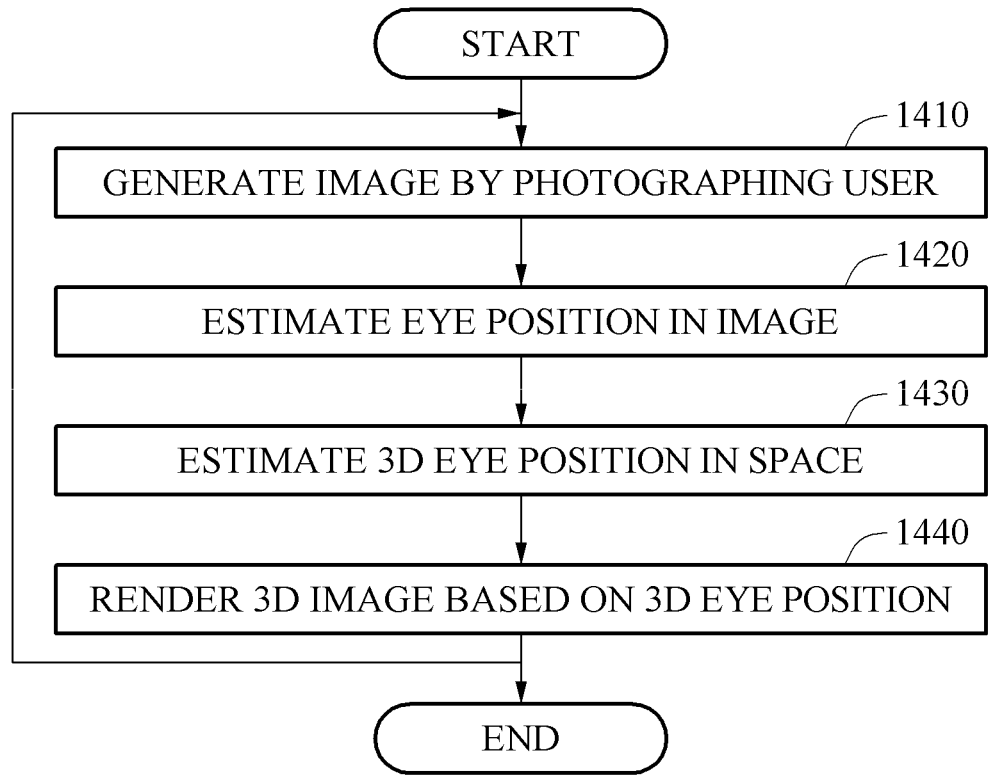

METHOD AND APPARATUS FOR DETERMINING INTERPUPILLARY DISTANCE (IPD)

CROSS-REFERENCE TO RELATED APPLICATION

This application claims priority benefit under 35 U.S.C. § 119 of Korean Patent Application No. 10-2016-0002405, filed on Jan. 8, 2016, at the Korean Intellectual Property Office, the entire contents of which are incorporated herein by reference.

BACKGROUND

1. Field

At least one example embodiment relates to a method and/or apparatus for determining an interpupillary distance (IPD). For example, at least some example embodiments relate to a method and/or apparatus for determining an IPD by analyzing an image obtained by photographing a user.

2. Description of the Related Art

An interpupillary distance (IPD) refers to a distance between pupils of a person. The IPD may be measured in advance for ophthalmology related eye procedures. A measuring apparatus, for example, a ruler, may be used to measure the IPD. When such a measuring apparatus is used, the IPD may be different depending on the person using the measuring apparatus.

Recently, the number of technical fields related to the display of three-dimensional (3D) images has increased such that research on methods of effectively transmitting 3D images for a user is being actively conducted. To effectively transmit a 3D image, the 3D image may be provided for each of a left eye and a right eye of the user. When an axis of an optical apparatus does not correspond to an axis of a gaze of the user, the user may experience dizziness.

SUMMARY

Some example embodiments relate to a method of determining an interpupillary distance (IPD).

In some example embodiments, the method may include outputting a source pattern to a display of an apparatus; capturing an image of a user gazing at the display; and determining an IPD of the user by analyzing the image.

In some example embodiments, the source pattern includes a background and at least one foreground having a color differing from a color of the background.

In some example embodiments, the at least one foreground has at least one of a rectangular form and a circular form.

In some example embodiments, the source pattern includes at least one of a two-dimensional (2D) pattern and a three-dimensional (3D) pattern.

In some example embodiments, the determining the IPD of the user includes detecting pupils of the user in the image; detecting a reflection pattern of peripheries of the pupils in the image; and determining the IPD based on the reflection pattern.

In some example embodiments, the determining the IPD based on the reflection pattern includes modeling a geometric model with respect to the display and eyeballs of the user based on positions of the detected pupils and a position of the reflection pattern.

In some example embodiments, a circumference of each of the eyeballs is generated based on a curvature of a cornea of a respective one of the eyeballs.

In some example embodiments, the modeling includes modeling the geometric model based on an intrinsic parameter of a camera configured to capture the image.

In some example embodiments, the determining the IPD based on the reflection pattern includes determining a 3D position of the reflection pattern; determining a position of a prediction pattern on the display based on the determined 3D position of the reflection pattern; and determining the IPD based on the position of the prediction pattern and a 3D position of the source pattern.

In some example embodiments, the apparatus is a 3D viewpoint tracking display apparatus, and the method further includes generating a stereoscopic image for a viewpoint of each of pupils based on the determined IPD; generating a verification image by photographing the user; and verifying an integrity of the IPD by analyzing an image reflected from an eye of the user using the verification image.

In some example embodiments, the verifying the integrity of the IPD includes determining whether the stereoscopic image is divided into a left image and a right image.

Some other example embodiments relate to a method of determining an interpupillary distance (IPD).

In some example embodiments, the method includes receiving an image of a user gazing at a source pattern output to a display of a terminal; and determining an IPD of the user by analyzing the image.

Some example embodiments relate to a non-transitory computer-readable medium storing program code that, when executed by a processor, configures the processor to determine an interpupillary distance (IPD).

Some other example embodiments relate to an apparatus configured to determine an interpupillary distance (IPD).

In some example embodiments, the apparatus includes a memory configured to store an image of a user gazing at a source pattern output to a display of a terminal; and a processor configured to determine an IPD of the user by analyzing the image.

In some example embodiments, the source pattern includes a background and at least one foreground having a color differing from a color of the background.

In some example embodiments, the processor is configured to, detect pupils of the user in the image, detect a reflection pattern of peripheries of the pupils in the image, and determine the IPD based on the reflection pattern.

In some example embodiments, the processor is configured to, determine a three-dimensional (3D) position of the reflection pattern, determine a position of a prediction pattern on the display based on the determined 3D position of the reflection pattern, and determine the IPD based on the position of the prediction pattern and a 3D position of the source pattern.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 13 is a flowchart illustrating another example of a method of determining an interpupillary distance (IPD) according to at least one example embodiment;

FIG. 14 is a flowchart illustrating an example of a method of rendering a three-dimensional (3D) image according to at least one example embodiment.

DETAILED DESCRIPTION

Figure 1:
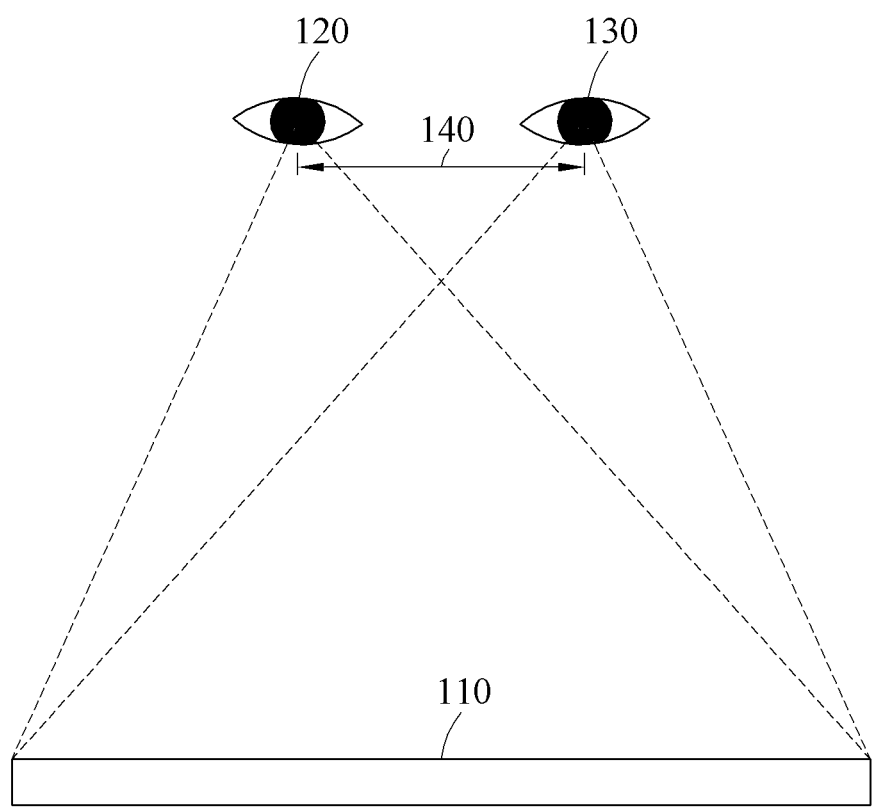
FIG. 1 illustrates an example of an interpupillary distance (IPD) used for a three-dimensional (3D) display according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be a computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Various example embodiments will now be described more fully with reference to the accompanying drawings in which some example embodiments are shown. In the drawings, the thicknesses of layers and regions are exaggerated for clarity.

FIG. 1 illustrates an example of an interpupillary distance (IPD) used for a three-dimensional (3D) display according to at least one example embodiment.

Referring to FIG. 1, in an example embodiment, a method of providing a 3D image may generate a single 3D image by rendering a left image and a right image. A display 110 provides the left image for a left eye 130 of a user and right image for a right eye 120 using a physical configuration. The physical configuration may be a lenticular lens or a barrier.

To appropriately provide the 3D image for the user, a position of the user may be accurately detected, and a distance between the left eye 130 and the right eye 120 may be accurately measured. In more detail, a distance 140 between a pupil of the left eye 130 and a pupil of the right eye 120 may need to be measured. The distance 140 between the pupil of the left eye 130 and the pupil of the right eye 120 is referred to as an interpupillary distance (IPD).

In another example, an accurate IPD may be desired for a medical purpose.

Detailed descriptions related to a method of determining an IPD will be provided with reference to FIGS. 2 through 13.

Figure 2:
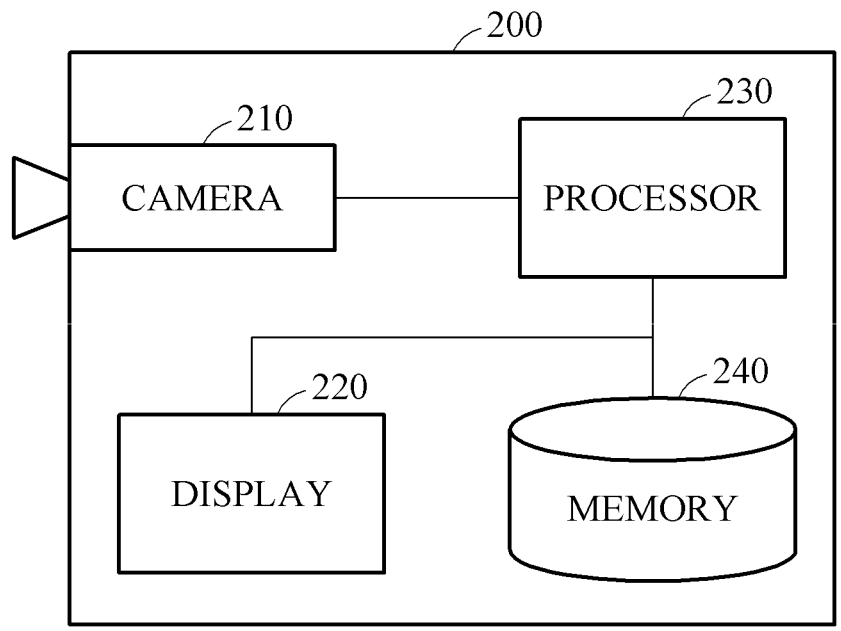
FIG. 2 is a block diagram illustrating an example of an apparatus for determining an interpupillary distance (IPD) according to at least one example embodiment.

FIG. 2 is a block diagram illustrating an example of an apparatus for determining an interpupillary distance (IPD) according to at least one example embodiment.

Referring to FIG. 2, the apparatus for determining an IPD, hereinafter also referred to as an apparatus 200, may include a camera 210, a display 220, a processor 230, and a memory 240.

The camera 210 generates an image obtained by photographing a user. For example, the camera 210 may photograph the user positioned near the apparatus 200. The display 220 outputs the image.

The processor 230 may be implemented by at least one semiconductor chip disposed on a printed circuit board. The processor 230 may be an arithmetic logic unit, a digital signal processor, a microcomputer, a field programmable array, a programmable logic unit, a microprocessor or any other device capable of responding to and executing instructions in a defined manner.

The processor 230 may be programmed with instructions that configure the processor 230 into a special purpose computer to process the image obtained by the camera 210 and process data stored in the memory 240.

For example, the processor 230 may be configured to calculate an interpupillary distance (IPD) between pupils of a user by modeling a geometric model based on a reflection of a source pattern reflected on the pupils and an intrinsic parameter of a camera. The processor 230 may use computed IPD to determine optical axes for a three-dimensional (3D) display such that the optical axes corresponds to the axes of a gaze of the eyes of the user.

The memory 240 may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The memory 240 stores the image obtained by the camera 210 and the data processed by the processor 230.

In some example embodiments, the apparatus 200 may also include a communicator (not shown). The communicator may include transmitters and/or receivers. The transmitters may include hardware and any necessary software for transmitting signals including, for example, data signals and/or control signals. The receivers may include hardware and any necessary software for receiving signals including, for example, data signals and/or control signals.

For example, the communicator may receive the data transmitted from an external apparatus and transmit the data processed in the apparatus 200 to the external apparatus.

Detailed descriptions related to the operation of the camera 210, the display 220, the processor 230, and the memory 240 will be provided with reference to FIGS. 3 through 13.

Figure 3:
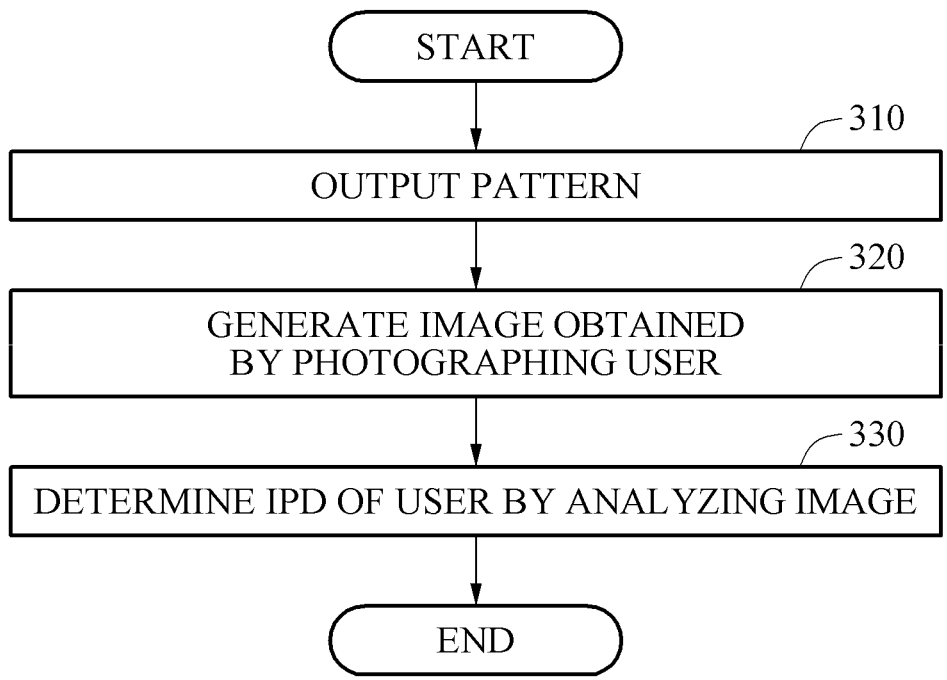
FIG. 3 is a flowchart illustrating an example of a method of determining an interpupillary distance (IPD) according to at least one example embodiment.

FIG. 3 is a flowchart illustrating an example of a method of determining an interpupillary distance (IPD) according to at least one example embodiment.

Referring to FIGS. 2 and 3, in operation 310, the processor 230 may output a pattern. For example, the processor 230 may output the pattern using the display 220. The display 220 may be any one of a smartphone, a tablet, a monitor, or a television. The display 220 is not limited to a predetermined method of outputting a light.

The pattern to be output may be predetermined. For example, the pattern may include a background and at least one foreground having a color differing from a color of the background. The at least one foreground may have at least one of a rectangular form and a circular form. Hereinafter, a foreground is also referred to as a feature point.

As another example, the pattern includes at least one of a two-dimensional (2D) pattern and a three-dimensional (3D) pattern. The 3D pattern may be a pattern in which each stereoscopic image is provided for a left eye and a right eye. For example, the 3D pattern may be a pattern in which a text indicating a left is provided for the left eye and a text indicating a right is provided for the right eye.

In subsequent operations, the pattern may be provided to differentiate feature points in the pattern since the pattern causes a reflection pattern reflected by an eye and it may be desirable to detect each reflection pattern.

The user gazes fixedly at the display 220 and fixes a gaze. Since the user gazes at the display 220, the pattern of the display 220 may be reflected by the eyes of the user. For example, the user may gaze at the display 220 before operation 310 is performed. As another example, the user may gaze at the display 220 to which the pattern is output after operation 310 is performed.

In operation 320, the processor 230 may obtain an image of the user gazing at the display 220 of the pattern. For example, the camera 210 may generate the image by photographing the user and provide the image to the processor 230. For example, the camera 210 may be embodied in the apparatus 200. As another example, the camera 210 may be an external apparatus separate from the apparatus 200.

In operation 330, the processor 230 may determine the IPD of the user by analyzing the image.

For example, to determine the IPD of the user, the processor 230 may detect pupils by analyzing the image, and detect, on peripheries of the pupils, the reflection pattern from the reflected pattern output to the display 220. The processor 230 may generate a geometric model with respect to the display 220 and eyeballs of the user based on a position of the reflection pattern, and calculate the IPD based on the geometric model.

Detailed descriptions related to a method of calculating an IPD based on a geometric model will be provided with reference to FIGS. 5 through 10.

Figure 4:
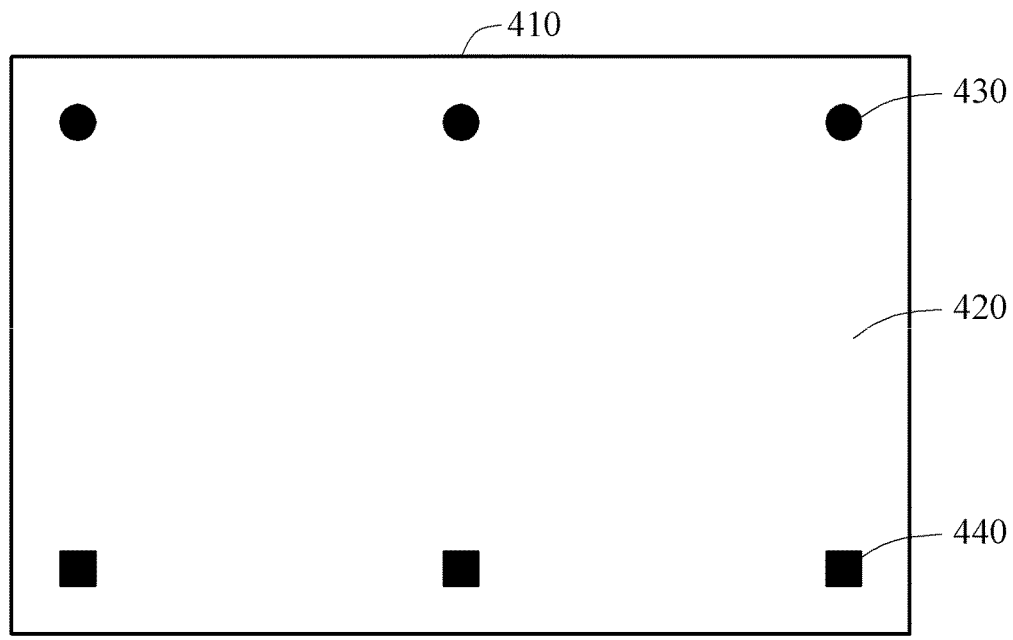
FIG. 4 illustrates an example of a pattern according to at least one example embodiment.

FIG. 4 illustrates an example of a pattern according to at least one example embodiment.

Referring to FIG. 4, in an example embodiment, a pattern 410 may include a plurality of feature points. The plurality of feature points, for example, a feature point 430 and a feature point 440, may include shapes such as a circle, a triangle, and a rectangle, and symbols. The plurality of feature points may be reflected by an eye of a user, and the processor 230 may generate a geometric model with respect to the display 220 and eyeballs of the user based on a position at which a reflection pattern appears.

Even though an interpupillary distance (IPD) may become more accurate as a number of the plurality of feature points increases, an amount of operation data may also increase. Thus, accuracy of the IPD and the amount of operation data according to the number of the feature points may have a trade-off relationship.

Figure 5:
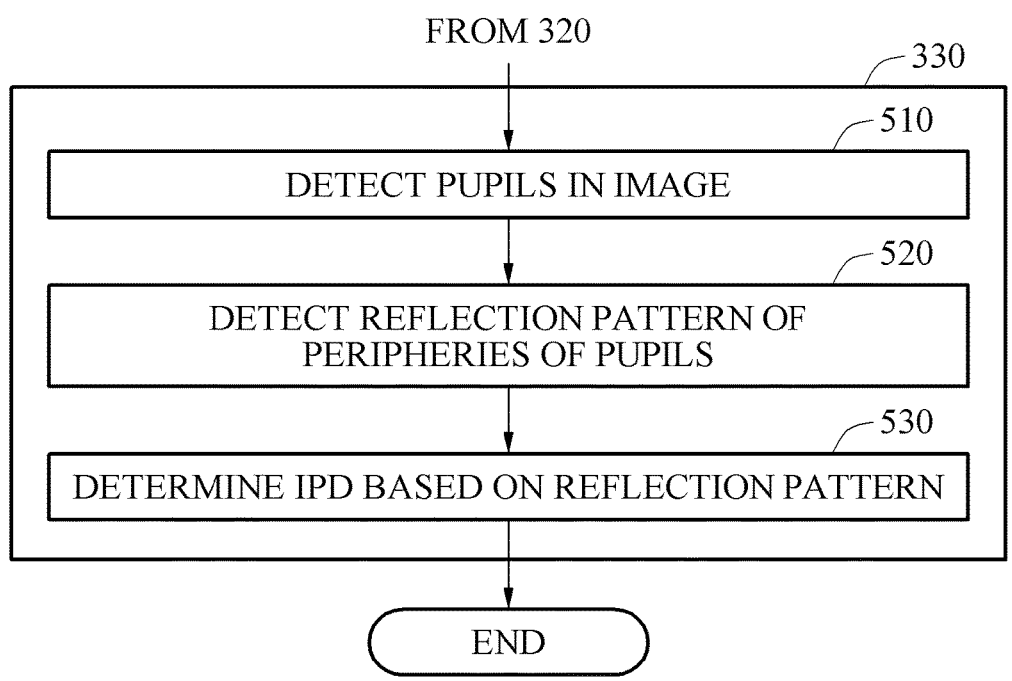
FIG. 5 is a flowchart illustrating an example of a method of determining an interpupillary distance (IPD) by analyzing an image according to at least one example embodiment.

FIG. 5 is a flowchart illustrating an example of a method of determining an interpupillary distance (IPD) by analyzing an image according to at least one example embodiment.

Referring to FIGS. 2, 3 and 5, while performing operation 330 described with reference to FIG. 3, the processor 230 may perform operations 510 through 530, discussed below. Hereinafter, a single eye is described for ease of description, though the following descriptions also refer to two eyes.

In operation 510, the processor 230 may detect pupils of the photographed user in an image. For example, the processor 230 may detect center coordinates of the pupil. A center of a detected pupil area may be determined as the center coordinates.

In operation 520, the processor 230 may detect a reflection pattern of peripheries of the pupils. When the reflection pattern is detected, the processor 230 may obtain coordinates of the reflection pattern. When a plurality of feature points of the pattern are provided, a plurality of detected reflection patterns may be provided.

In operation 530, the processor 230 may determine the IPD based on the detected reflection pattern. For example, to determine the IPD, the processor 230 may model a geometric model with respect to the display 220 and eyeballs of a user based on positions of the detected pupils and a position of the reflection pattern. The processor 230 may model the geometric model based on an intrinsic parameter of the camera 210.

The processor 230 may determine a correlation between desired (or, alternatively, predetermined) positions in the geometric model based on the geometric model. When the correlation is determined, the processor 230 may determine the IPD. Related descriptions related to a method of determining an IPD based on a geometric model will be provided with reference to FIGS. 7 through 9.

Figure 6:
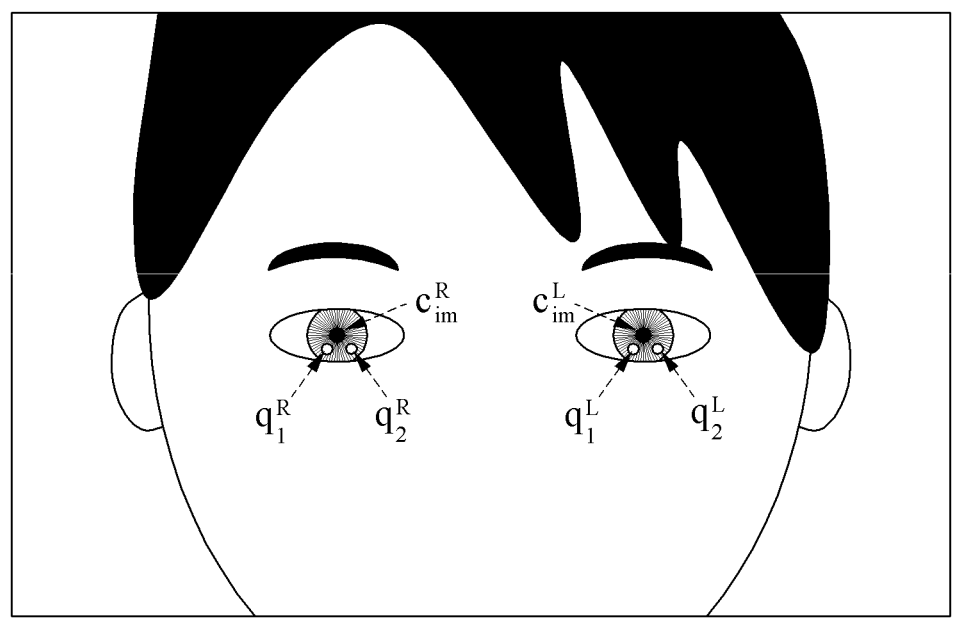
FIG. 6 illustrates an example of detected pupils and a reflection pattern according to at least one example embodiment.

FIG. 6 illustrates an example of detected pupils and a reflection pattern according to at least one example embodiment.

Referring to FIG. 6, in an image 600 obtained by photographing a user, the processor 230 may determine pupils of the user and determine center coordinates $c^R_{im}$ and $c^L_{im}$ of the detected pupils. $c^R_{im}$ represents center coordinates of a right pupil, and $c^L_{im}$ represents center coordinates of a left pupil.

The processor 230 may detect a reflection pattern of peripheries of the pupils. A periphery of a pupil may be part of a cornea. When a plurality of feature points of the pattern are provided, the processor 230 may detect a plurality of reflection patterns. For example, when a number of feature points is two, positions $q^L_1$ and $q^L_2$ of reflection patterns may be detected on a periphery of a left pupil, and positions $e_1$ and $q^R_2$ of reflection patterns may be detected on a periphery of a right pupil.

Figure 7:
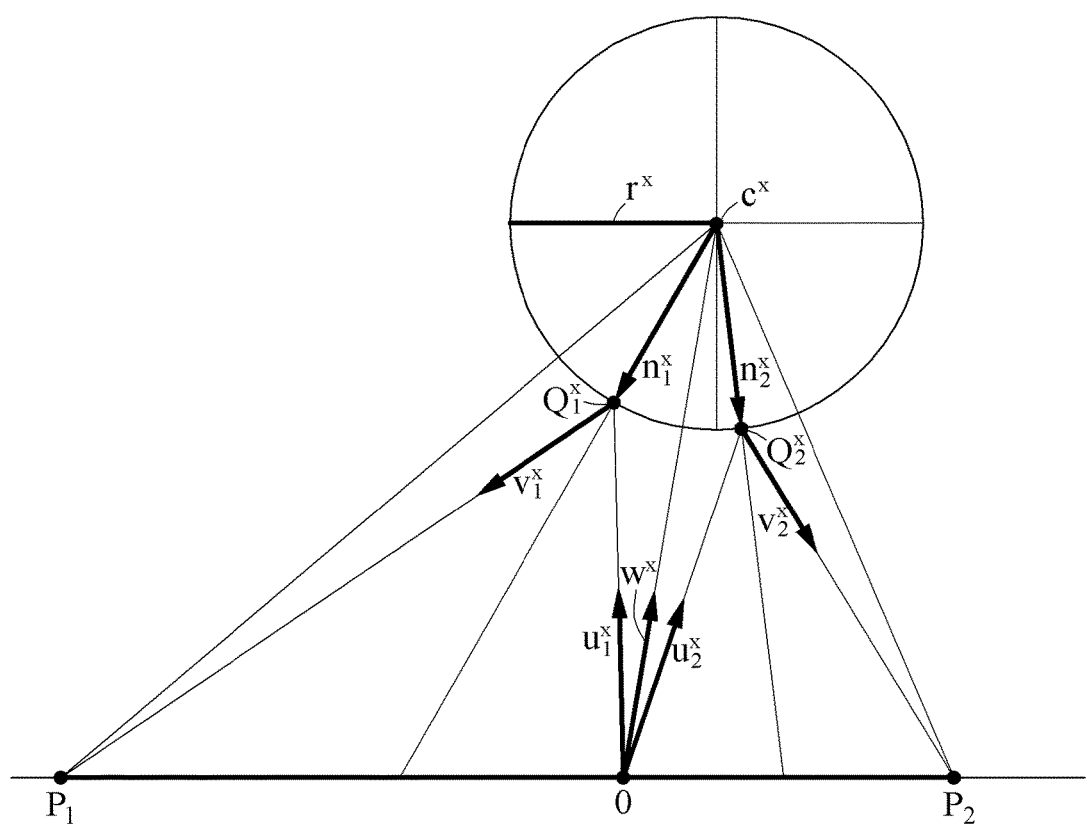
FIG. 7 illustrates an example of a geometric model with respect to a display and eyeballs according to at least one example embodiment.

A geometric model similar to that of FIG. 7 may be generated based on the center coordinates $c^R_{im}$ and $c^L_{im}$ of the detected pupils and the positions $q^L_1$, $q^L_2$ $q^R_1$, and $q^R_2$ of the reflection patterns on the periphery of the pupils.

FIG. 7 illustrates an example of a geometric model with respect to a display and eyeballs according to at least one example embodiment.

Referring to FIG. 7, $P_1$ and $P_2$ of a model 700 indicate three-dimensional (3D) coordinates of feature points of a pattern, and camera coordinates O indicate 3D coordinates of the camera 210. The camera coordinates O may indicate an origin of a 3D coordinate system. The 3D coordinates and the camera coordinates O of the feature points may be obtained in advance. However, example embodiments are not limited thereto. For example, in some example embodiments, the 3D coordinates and the camera coordinates O may be obtained at runtime.

A circle in the model 700 indicates an eyeball, and a circumference of the eyeball may be determined based on a degree of curvature of a cornea. The eyeball may have a radius $r^x$ based on center coordinates $C^x$ of the eyeball, and the eyeball may be optically considered to be a spherical reflector. The center coordinates $C^x$ of the eyeball may correspond to center coordinates $c^x_{im}$ of a pupil, where x indicates a left L or a right R eye.

The processor 230 may calculate a unit vector $w^x$ from a position of the camera 210 to the center coordinates $C^x$ of the eyeball based on the detected center coordinates $c^x_{im}$ of the pupil and an intrinsic parameter K of the camera 210. The intrinsic parameter K of the camera 210 may include a focal length, a principle point, and/or an optical aberration, and may be expressed in inverse form as $K^{-1}$.

In some example embodiments, the processor 230 may calculate the unit vector $w^x$ from the position of the camera 210 to the center coordinates $C^x$ of the eyeball using Equation 1. The unit vector $w^x$ may be a unit vector of a back-propagated beam of the detected center coordinates $c^x_{im}$ of the pupil.

$$w^x = \frac{K^{-1} C^x_{im}}{\|K^{-1} C^x_{im}\|} \quad \text{[Equation 1]}$$

The processor 230 may calculate a unit vector $u^x_n$ from the position of the camera 210 to coordinates $Q^x_n$ of a reflection pattern based on a position $q^x_n$ of the detected reflection pattern and the intrinsic parameter of the camera 210. The coordinates $Q^x_n$ of the reflection pattern may be 3D coordinates.

The processor 230 may calculate the unit vector $u^x_n$ from the position of the camera 210 to the coordinates $Q^x_n$ of the reflection pattern using Equation 2. The $u^x_n$ may be a unit vector of a back-propagated beam of the coordinates $Q^x_n$ of the reflection pattern. When a number of detected reflection patterns is N, a plurality of unit vectors, for example, the unit vector $u^x_n$, may be calculated. N is a natural number and n is a number of 1 through N.

$$u^x_n = \frac{K^{-1} q^x_n}{\|K^{-1} q^x_n\|} \quad \text{[Equation 2]}$$

The processor 230 may obtain the coordinates $Q^x_n$ of the reflection pattern by multiplying the unit vector $u^x_n$ by a scalar value $\xi^x_n$. For example, the coordinates $Q^x_n$ of the reflection pattern may be calculated using Equation 3. The scalar value $\xi^x_n$ indicates a distance from the camera coordinates O to the coordinates $Q^x_n$ of the reflection pattern.

$$Q_n^x = \xi_n^x u_n^x \quad \text{[Equation 3]}$$

The processor 230 may obtain the center coordinates $C^x$ of the eyeball by multiplying the unit vector $w^x$ by a scalar value $d^x$. For example, the center coordinates $C^x$ of the eyeball may be calculated using Equation 4.

$$C^x = d^x w^x \quad \text{[Equation 4]}$$

The radius $r^x$ of the eyeball may be similar (or, alternatively, identical) to a distance between the center coordinates $C^x$ of the eyeball and the coordinates $Q^x_n$ of the reflection pattern. Therefore, the processor 230 may calculate the radius $r^x$ of the eyeball using Equation 5.

$$r^x = \|\xi_n^x - d^x\| \quad \text{[Equation 5]}$$

The processor 230 may calculate the distance $\xi^x_n$ from the camera coordinates O to the coordinates $Q^x_n$ of the reflection pattern may using Equation 6, which is obtained using Equation 4 and Equation 5.

$$\xi_n^x = d^x(u_n^{xT} w^x) - \sqrt{r^{x^2} - d^{x^2}(1-(u_n^{xT} w^x)^2)} \quad \text{[Equation 6]}$$

Based on Equation 6, the processor 230 may calculate the coordinates $Q^x_n$ of the reflection pattern using Equation 7.

$$Q_n^x = d^x(u_n^{xT} w^x)u_n^x - \sqrt{r^{x^2} - d^{x^2}(1-(u_n^{xT} w^x)^2)} u_n^x \quad \text{[Equation 7]}$$

So a beam from a feature point $P_n$ of the pattern is toward the camera coordinates O, the beam from the feature point $P_n$ of the pattern may be reflected from the coordinates $Q^x_n$ of the reflection pattern. Since the eyeball is set to be the circle, the beam from the feature point $P_n$ of the pattern may be reflected from a tangent line of the coordinates $Q^x_n$ of the reflection pattern. Detailed descriptions related to a model of the feature point $P_n$ of the pattern, the coordinates $Q^x_n$ of the reflection pattern, and the camera coordinates O will be provided with reference to FIG. 8.

Figure 8:
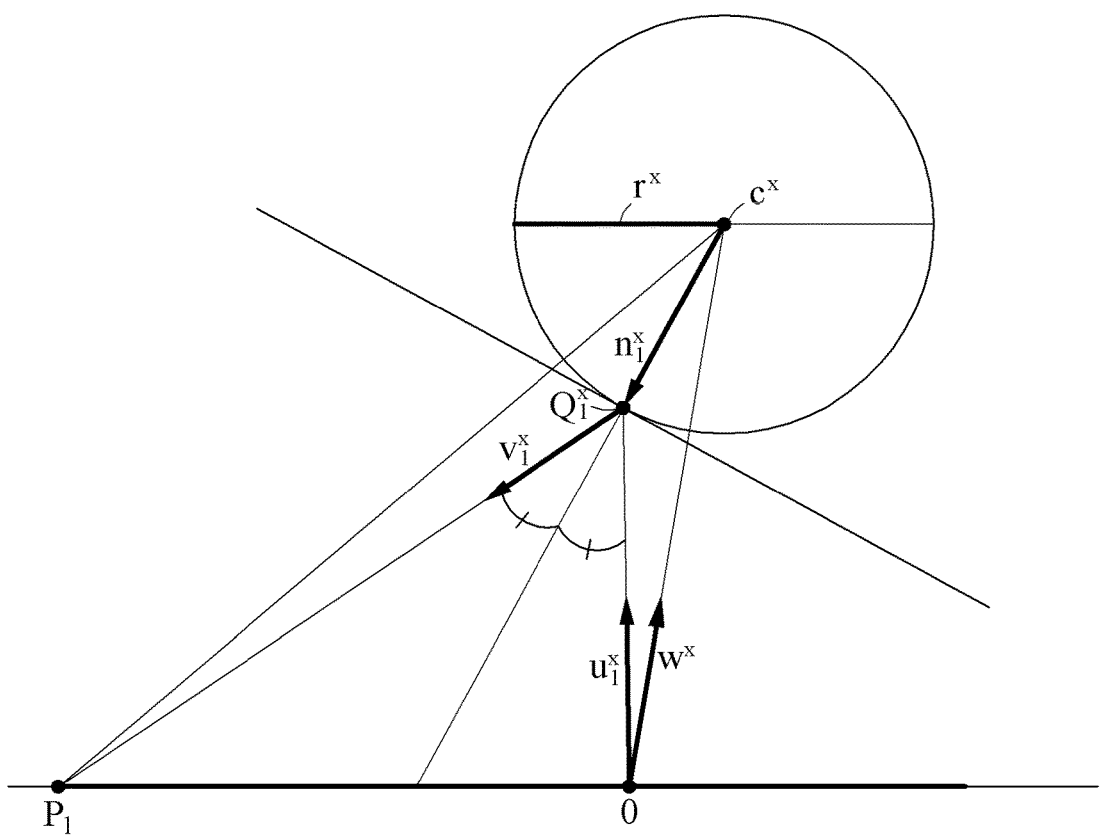
FIG. 8 illustrates an example of geometrically illustrated spherical reflection according to at least one example embodiment.

FIG. 8 illustrates an example of a geometrically represented spherical reflection according to at least one example embodiment.

Referring to FIG. 8, a relationship between a feature point $P_n$ of a pattern, coordinates $Q^x_n$ of a reflection pattern, and camera coordinates O is a relationship of the spherical reflection. A normal vector $n^x_n$ for the coordinates $Q^x_n$ of the reflection pattern is defined as Equation 8.

$$n_n^x = \frac{Q_n^x - C^x}{r^x} \quad \text{[Equation 8]}$$

The processor 230 may calculate a unit vector from the coordinates $Q^x_n$ of the reflection pattern to the feature point $P_n$ of the pattern calculated based on a unit vector $u^x_n$ and the normal vector $n^x_n$ using Equation 9. I may represent a diagonal matrix.

$$v_n^x = (I - n_n^x n_n^{xT}) u_n^x \quad \text{[Equation 9]}$$

The processor 230 may calculate coordinates of the feature point $P_n$ using Equation 10. $\tau^x_n$ may be a distance between the feature point $P_n$ and the coordinates $Q^x_n$ of the reflection pattern. An initial value of $\tau^x_n$ may be set to be a desired (or, alternatively, a predetermined) value, and a value of $\tau^x_n$ may be adjusted to satisfy Equation 10.

$$P_n = \tau^x_n v^x_n \quad \text{[Equation 10]}$$

To obtain all values of a model 800, the processor 230 may determine a scalar value $d^x$ and a radius $r^x$ of an eyeball. When coordinates of the feature points calculated using Equations 4 through 10 are $P'_n(n=1,2,\ldots,N)$ and actual positions of the feature points are $P_n(n=1,2,\ldots,N)$ the scalar value $d^x$ may be determined such that a difference between the calculated coordinates of the feature points and the actual positions of the feature points is minimized. The calculated coordinates of the feature points may be a position of a prediction pattern.

When the radius $r^x$ of the eyeball is set in advance, the scalar value $d^x$ may be an unknown number. For example, the processor 230 may set the radius $r^x$ of the eyeball to be an average eyeball radius. The processor 230 may calculate the scalar value $d^x$ and the radius $r^x$ of the eyeball using Equation 11.

$$d^x, r^x = \mathrm{argmin} \sum_{n=1}^{N} \|P'n - P_n\| \quad \text{[Equation 11]}$$

Three-dimensional (3D) coordinates $L^x$ of a pupil may indicate a point at which the eyeball meets a beam from the origin of the camera coordinates O to coordinates $C^x$ of a center of the eyeball. The processor 230 may calculate the coordinates $L^x$ of the point in which the eyeball meets the beam using Equation 12.

$$L^x = w^x(d^x - r^x) \quad \text{[Equation 12]}$$

Figure 9:
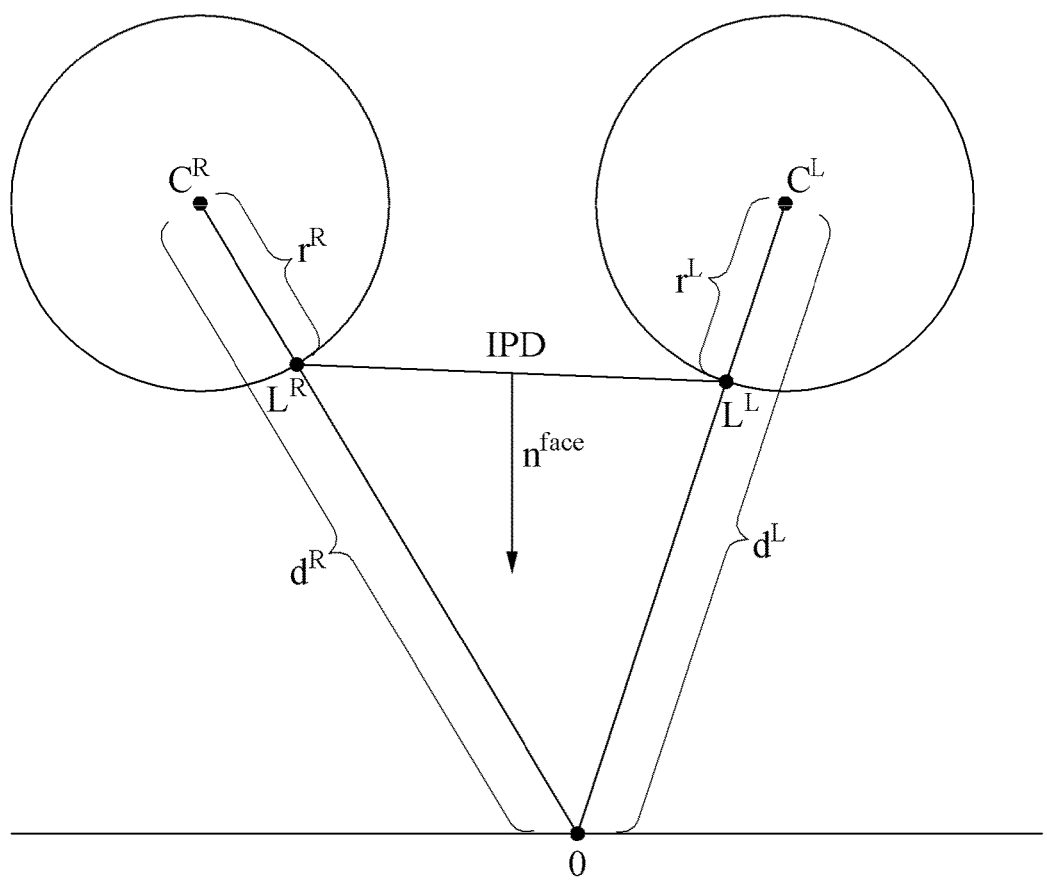
FIG. 9 illustrates an example of an interpupillary distance (IPD) calculated based on a geometric model according to at least one example embodiment.

When 3D coordinates $L^L$ of a left pupil and 3D coordinates $L^R$ of a right pupil are calculated, the model 800 may be simplified to a model 900 of FIG. 9.

FIG. 9 illustrates an example of an interpupillary distance (IPD) calculated based on a geometric model according to at least one example embodiment.

The processor 230 may calculate an interpupillary distance (IPD) based on 3D coordinates $L^L$ of a left pupil and 3D coordinates of $L^R$ of a right pupil using Equation 13.

$$\mathrm{IPD} = \|L^L - L^R\| \quad \text{[Equation 13]}$$

The processor may calculate a normal vector $n^{face}$ of a face using Equation 14.

$$n^{face} = \frac{(L^L - L^R) \times (L^L \times L^R)}{\|(L^L - L^R) \times (L^L \times L^R)\|} \quad \text{[Equation 14]}$$

Figure 10:
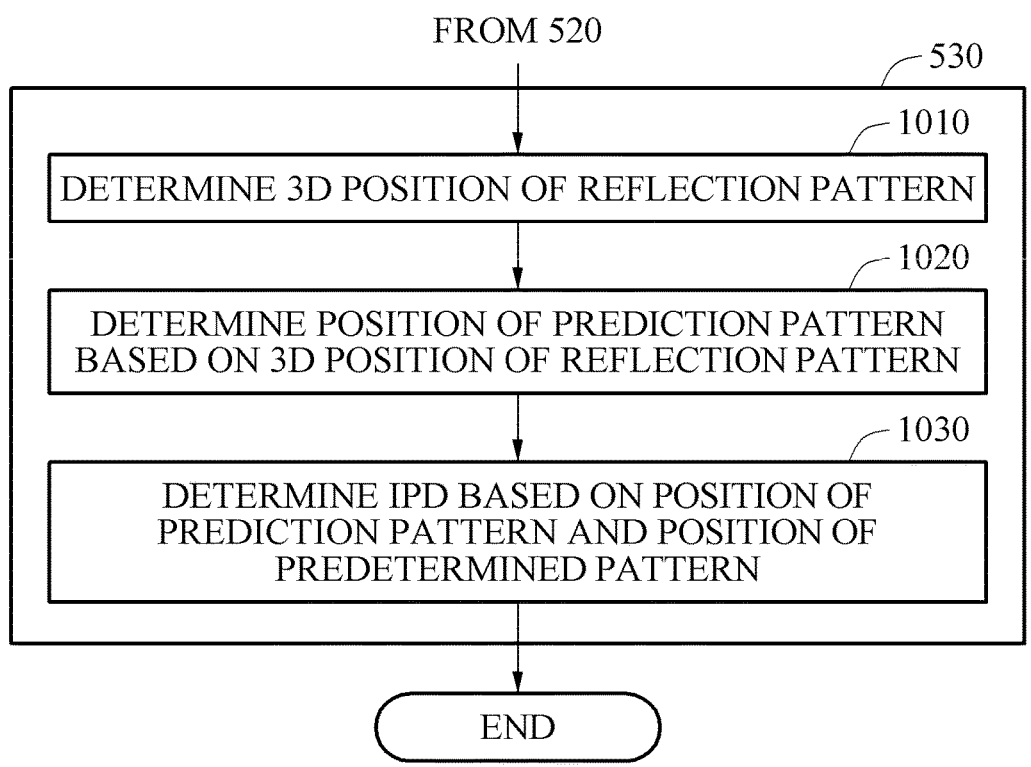
FIG. 10 is a flowchart illustrating an example of a method of determining an interpupillary distance (IPD) based on a reflection pattern according to at least one example embodiment.

FIG. 10 is a flowchart illustrating an example of a method of determining an interpupillary distance (IPD) based on a reflection pattern according to at least one example embodiment.

Referring to FIGS. 2, 5 and 10, while performing operation 530 described with reference to FIG. 5, the processor 230 may perform operations 1010 through 1030, discussed below.

In operation 1010, the processor 230 may determine a three-dimensional (3D) position of a reflection pattern. The 3D position may be 3D coordinates with respect to the model 700.

In operation 1020, the processor 230 may determine a position of a prediction pattern based on the 3D position of the reflection pattern. The position of the prediction pattern may be coordinates $P'_n(n=1,2,\ldots,N)$ of the feature points calculated using Equations 4 through 10.

In operation 1030, the processor 230 may determine an IPD based on the position of the prediction pattern and a position of a known (or, alternatively, a predetermined) pattern. The position of the known (or, alternatively, the predetermined) pattern may be actual positions $P_n$ $(n=1,2,\ldots,N)$ of the feature points. For example, the IPD may be determined such that a difference between the position of the prediction pattern and a position of the known (or, alternatively, the predetermined) pattern is minimized.

Figure 11:
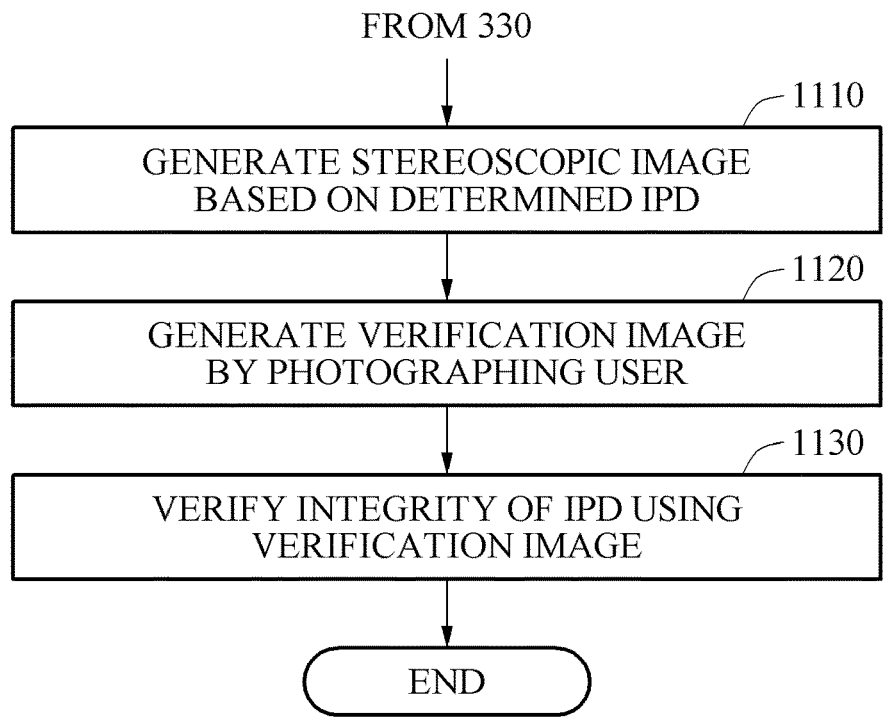
FIG. 11 is a flowchart illustrating an example of method of verifying an integrity of an interpupillary distance (IPD) according to at least one example embodiment.

FIG. 11 is a flowchart illustrating an example of method of verifying an integrity of an interpupillary distance (IPD) according to at least one example embodiment.

Referring to FIGS. 2, 3 and 11, in an example embodiment, the apparatus 200 is a three-dimensional (3D) viewpoint tracking display apparatus. When the apparatus 200 is the viewpoint tracking display apparatus, the processor 230 therein, when determining the IPD, the processor 230 may further perform operations 1110 through 1130, discussed below.

In operation 1110, the processor 230 may generate a stereoscopic image for a viewpoint of each of the pupils based on the determined IPD. When the stereoscopic image is rendered, a different left image and right image may be used. The processor 230 may output the generated stereoscopic image through the display 220.

In operation 1120, the processor 230 may generate a verification image by photographing a user. For example, under control of the processor 230, the camera 210 may capture the verification image by photographing the user such that the verification image may be similar to the image 600 of FIG. 6. Before the user is photographed, the user may gaze at the display 220 or the camera 210.

In operation 1130, the processor 230 may verify an integrity of the IPD by analyzing an image reflected from an eye of the user using the verification image. For example, a pupil of the user may be detected and a reflection image appearing on a periphery of the detected pupil may be detected. When the detected reflection image is divided into the left image and the right image, the determined IPD may be verified to be proper.

Figure 12:
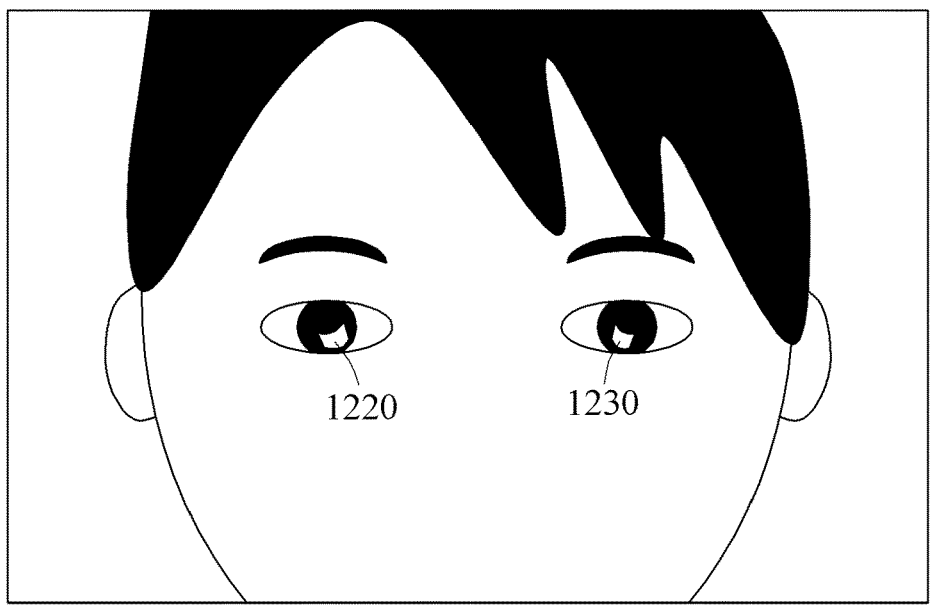
FIG. 12 illustrates an example of a verification image according to at least one example embodiment.

FIG. 12 illustrates an example of a verification image according to at least one example embodiment.

Referring to FIG. 12, the processor 230 may verify whether a determined interpupillary distance (IPD) is proper by analyzing a first reflection image 1220 and a second reflection image 1230 included in a verification image 1210. The first reflection image 1220 may be an image to which an image provided for a right eye of a stereoscopic image is reflected, and the second reflection image 1230 may be an image to which an image provided for a left eye of the stereoscopic image is reflected.

For example, the stereoscopic image may be rendered as a red left image and a blue left image. When the processor 230 detects a red image as a first reflection image and a blue image as a second reflection image, the processor 230 may verify that the determined IPD is proper.

FIG. 13 is a flowchart illustrating another example of a method of determining an interpupillary distance (IPD) according to at least one example embodiment.

Referring to FIGS. 2 and 13, in an example embodiment, the method of determining an IPD may be performed even when the apparatus 200 does not photograph an image.

For example, when an image of a user and an intrinsic parameter of a camera photographing the image are obtained from an outside source, the apparatus 200 may determine the IPD by analyzing the image received from the outside source.

Therefore, in some example embodiments, the apparatus 200 may include the communicator, the processor 230, and the memory 240 but may not include the camera 210 and/or the display 220.

In operation 1310, the processor 230 may receive an image of the user. A camera associated with a terminal of the outside source may obtain the image by photographing the user gazing at a desired (or, alternatively, a predetermined) pattern output to a display of the terminal.

The processor 230 may receive the image and an intrinsic parameter of the camera from the terminal photographing the image. The terminal photographing the image may include a television, a portable terminal, and a piece of medical equipment. The received image may be stored in the memory 240.

In operation 1320, the processor 230 may determine the IPD of the user by analyzing the image. Repeated descriptions will be omitted for increased clarity and conciseness because the descriptions provided with reference to operation 330 are also applicable to operation 1320.

Additionally, information on the determined IPD may be transmitted to the terminal.

FIG. 14 is a flowchart illustrating an example of a method of rendering a three-dimensional (3D) image according to at least one example embodiment.

Referring to FIG. 14, in an example embodiment, a method of estimating an interpupillary distance (IPD) of a user may be used for a method of generating a virtual image using an actual image.

For example, the apparatus 200 may be included in a three-dimensional (3D) image rendering apparatus. The 3D image rendering apparatus may perform Operations 1410 through 1440, discussed below In operation 1410, the 3D image rendering apparatus may generate an image by photographing a user. For example, the image obtained by photographing the user may be used to verify whether the user exists. Operation 1410 may be performed when a position of the user is changed.

In operation 1420, the 3D image rendering apparatus may estimate an eye position in the image. A face of the user may be detected in the image and the eye position of the user may be estimated based on the detected face.

In operation 1430, the 3D image rendering apparatus may determine a 3D eye position in a space based on the estimated eye position of the user.

When the eye position in the image is estimated, the 3D image rendering apparatus may photograph the eye of the user based on the estimated eye position.

The 3D image rendering apparatus may estimate the IPD of the user based on the image obtained by photographing the eye of the user. Repeated descriptions will be omitted for increased clarity and conciseness because the descriptions provided with reference to FIGS. 2 through 13 are also applicable to the method of estimating the IPD of the user.

The 3D eye position in the space may be estimated based on the estimated IPD of the user. The space may be a 3D space formed based on a position of the 3D image rendering apparatus and a position of the user.

In operation 1440, the 3D image rendering apparatus may render a 3D image based on the 3D eye position. For example, the 3D image may be rendered to provide a virtual image for the 3D eye position using a reference image. A 3D image corresponding to a left eye and a 3D image corresponding to a right eye may be generated. A panel image may be generated based on the generated 3D images and a pattern output to a display. The display outputs the panel image thereby providing the 3D images for the user.

Figure 15:
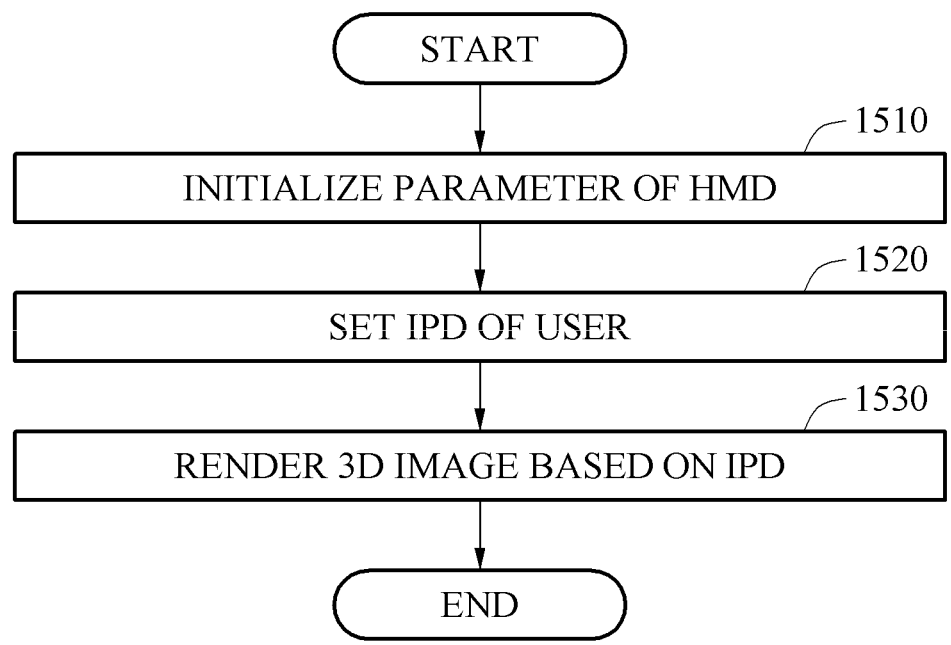
FIG. 15 is a flowchart illustrating another example of a method of rendering a three-dimensional (3D) image according to at least one example embodiment.

FIG. 15 is a flowchart illustrating another example of a method of rendering a three-dimensional (3D) image according to at least one example embodiment.

Referring to FIGS. 2 and 15, a method of estimating an interpupillary distance (IPD) of a user may be used for a method of providing a three-dimensional (3D) image for the user using a head mounted display (HMD).

For example, the apparatus 200 may be included in the HMD. The HMD may perform operations 1510 through 1530, discussed below.

In operation 1510, the HMD may initialize a parameter of the HMD. For example, the parameter for the IPD of the user may be initialized when the user wears the HMD.

In operation 1520, the HMD may set the IPD of the user. Repeated descriptions will be omitted for increased clarity and conciseness because the descriptions provided with reference to FIGS. 2 through 13 are also applicable to the method of setting the IPD of the user.

In operation 1530, the HMD may render the 3D image based on the set IPD. The rendered 3D image may be provided for the user through a display of the HMD.

The units and/or modules described herein may be implemented using hardware components and software components. For example, the hardware components may include microphones, amplifiers, band-pass filters, audio to digital converters, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is singular; however, one skilled in the art will appreciate that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method implemented by an apparatus to determine an interpupillary distance (IPD), the method comprising:
   outputting a source pattern to a display of the apparatus;
   capturing an image of a user gazing at the display; and
   determining the IPD of the user by analyzing the image to,
      detect pupils of the user in the image,
      detect a reflection pattern of peripheries of the pupils in the image, the reflection pattern corresponding to the source pattern, and
      determine the IPD based on positions of the detected pupils and a position of the reflection pattern.

2. The method of claim 1, wherein the source pattern includes a background and at least one foreground having a color differing from a color of the background.

3. The method of claim 2, wherein the at least one foreground has at least one of a rectangular form and a circular form.

4. The method of claim 2, wherein the source pattern includes at least one of a two-dimensional (2D) pattern and a three-dimensional (3D) pattern.

5. The method of claim 1, wherein the determining the IPD based on positions of the detected pupils and the position of the reflection pattern comprises: modeling a geometric model with respect to the display and the eyeballs of the user based on the positions of the detected pupils and the position of the reflection pattern.

6. The method of claim 5, wherein a circumference of each of the eyeballs is generated based on a curvature of a cornea of a respective one of the eyeballs.

7. The method of claim 5, wherein the modeling comprises:
   modeling the geometric model based on an intrinsic parameter of a camera configured to capture the image.

8. The method of claim 1, wherein the determining the IPD based on positions of the detected pupils and the position of the reflection pattern comprises:
   determining a 3D position of the reflection pattern;
   determining a position of a prediction pattern on the display based on the determined 3D position of the reflection pattern; and
   determining the IPD based on the position of the prediction pattern and a 3D position of the source pattern.

9. The method of claim 1, wherein the apparatus is a 3D viewpoint tracking display apparatus, and the method further comprises:
   generating a stereoscopic image for a viewpoint of each of pupils based on the determined IPD;
   generating a verification image by photographing the user; and
   verifying an integrity of the IPD by analyzing an image reflected from an eye of the user using the verification image.

10. The method of claim 9, wherein the verifying the integrity of the IPD comprises:
   determining whether the stereoscopic image is divided into a left image and a right image.

11. A non-transitory computer-readable medium storing program code that, when executed by a processor, performs functions according to the method of claim 1.

12. A method implemented by an apparatus to determine an interpupillary distance (IPD), the method comprising:
   receiving an image of a user gazing at a source pattern output to a display of a terminal; and
   determining the IPD of the user by analyzing the image to,
      detect pupils of the user in the image,
      detect a reflection pattern of peripheries of the pupils in the image, the reflection pattern corresponding to the source pattern, and
      determine the IPD based on positions of the detected pupils and a position of the reflection pattern.

13. An apparatus configured to determine an interpupillary distance (IPD), the apparatus comprising:
   a memory configured to store an image of a user gazing at a source pattern output to a display of a terminal; and
   a processor configured to,
      determine the IPD of the user by analyzing the image to,
         detect pupils of the user in the image,
         detect a reflection pattern of peripheries of the pupils in the image,
         the reflection pattern corresponding to the source pattern, and
         determine the IPD based on positions of the detected pupils and a position of the reflection pattern.

14. The apparatus of claim 13, wherein the source pattern includes a background and at least one foreground having a color differing from a color of the background.

15. The apparatus of claim 13, wherein the processor is configured to,
   determine a three-dimensional (3D) position of the reflection pattern, determine a position of a prediction pattern on the display based on the determined 3D position of the reflection pattern, and determine the IPD based on the position of the prediction pattern and a 3D position of the source pattern.

* * * * *